US008173107B2

(12) United States Patent
Rabinowitz et al.

(10) Patent No.: US 8,173,107 B2
(45) Date of Patent: *May 8, 2012

(54) DELIVERY OF ANTIPSYCHOTICS THROUGH AN INHALATION ROUTE

(75) Inventors: Joshua D. Rabinowitz, Princeton, NJ (US); Alejandro C. Zaffaroni, Atherton, CA (US)

(73) Assignee: Alexza Pharmaceuticals, Inc., Mountain View, CA (US)

( * ) Notice: Subject to any disclaimer, the term of this patent is extended or adjusted under 35 U.S.C. 154(b) by 172 days.

This patent is subject to a terminal disclaimer.

(21) Appl. No.: 12/413,339

(22) Filed: Mar. 27, 2009

(65) Prior Publication Data

US 2009/0246147 A1    Oct. 1, 2009

Related U.S. Application Data

(63) Continuation of application No. 11/488,932, filed on Jul. 18, 2006, now Pat. No. 7,601,337, which is a continuation of application No. 10/750,303, filed on Dec. 30, 2003, now Pat. No. 7,078,020, which is a continuation of application No. 10/152,639, filed on May 20, 2002, now Pat. No. 6,716,416.

(60) Provisional application No. 60/294,203, filed on May 24, 2001, provisional application No. 60/317,479, filed on Sep. 5, 2001.

(51) Int. Cl.
*A61K 9/12* (2006.01)
*A61K 9/14* (2006.01)
*A61M 15/00* (2006.01)

(52) U.S. Cl. ............ 424/45; 424/46; 424/434; 424/489; 424/499; 514/958; 128/200.14; 128/200.24; 128/203.15

(58) Field of Classification Search ............... 424/45, 424/46, 434, 489, 499; 514/958; 128/200.14, 128/200.24, 203.15
See application file for complete search history.

(56) References Cited

U.S. PATENT DOCUMENTS

| | | |
|---|---|---|
| 2,902,484 A | 9/1959 | Horclois |
| 3,219,533 A | 11/1965 | Mullins |
| 3,560,607 A | 2/1971 | Hartley et al. |
| 3,949,743 A | 4/1976 | Shanbrom |
| 3,982,095 A | 9/1976 | Robinson |
| 4,141,369 A | 2/1979 | Burruss |
| 4,183,912 A | 1/1980 | Rosenthale |
| RE30,285 E | 5/1980 | Babington |
| 4,303,083 A | 12/1981 | Burruss, Jr. |
| 4,474,191 A | 10/1984 | Steiner |
| 4,484,576 A | 11/1984 | Albarda |
| 4,566,451 A | 1/1986 | Badewien |
| 4,605,552 A | 8/1986 | Fritschi |
| 4,708,151 A | 11/1987 | Shelar |
| 4,734,560 A | 3/1988 | Bowen |
| 4,735,217 A | 4/1988 | Gerth et al. |
| 4,819,665 A | 4/1989 | Roberts et al. |
| 4,848,374 A | 7/1989 | Chard et al. |
| 4,853,517 A | 8/1989 | Bowen et al. |
| 4,895,719 A | 1/1990 | Radhakrishnun et al. |
| 4,906,417 A | 3/1990 | Gentry |
| 4,917,119 A | 4/1990 | Potter et al. |
| 4,924,883 A | 5/1990 | Perfetti et al. |
| 4,941,483 A | 7/1990 | Ridings et al. |
| 4,963,289 A | 10/1990 | Ortiz et al. |
| 5,042,509 A | 8/1991 | Banerjee et al. |
| 5,049,389 A | 9/1991 | Radhakrishnun |
| 5,060,671 A | 10/1991 | Counts et al. |
| 5,099,861 A | 3/1992 | Clearman et al. |
| 5,135,009 A | 8/1992 | Muller et al. |
| 5,144,962 A | 9/1992 | Counts et al. |
| 5,146,915 A | 9/1992 | Montgomery |
| 5,224,498 A | 7/1993 | Deevi et al. |
| 5,240,922 A | 8/1993 | O'Neill |
| 5,284,133 A | 2/1994 | Burns et al. |
| 5,345,951 A | 9/1994 | Serrano et al. |
| 5,366,770 A | 11/1994 | Wang |
| 5,388,574 A | 2/1995 | Ingebrethsen |
| 5,456,247 A | 10/1995 | Shilling et al. |
| 5,511,726 A | 4/1996 | Greenspan et al. |
| 5,544,646 A | 8/1996 | Lloyd et al. |
| 5,564,442 A | 10/1996 | MacDonald et al. |
| 5,592,934 A | 1/1997 | Thwaites |

(Continued)

FOREIGN PATENT DOCUMENTS

EP    0 358 114    3/1990

(Continued)

OTHER PUBLICATIONS

U.S. Appl. No. 11/687,466, filed Mar. 16, 2007, Zaffaroni et al.
U.S. Appl. No. 12/211,247, filed Sep. 16, 2008, Sharma et al.
U.S. Appl. No. 12/211,554, filed Sep. 16, 2008, Sharma et al.
U.S. Appl. No. 12/211,628, filed Sep. 16, 2008, Lei et al.
U.S. Appl. No. 12/352,582, filed Jan. 12, 2009, Hale et al.
U.S. Appl. No. 12/471,070, filed May 22, 2009, Hale et al.
U.S. Appl. No. 12/474,680, filed May 29, 2009, Cross et al.
Office Action mailed Jan. 26, 2007 with respect to U.S. Appl. No. 10/057,198.
Office Action mailed Jul. 3, 2006 with respect to U.S. Appl. No. 10/057,198.

(Continued)

*Primary Examiner* — Mina Haghighatian
(74) *Attorney, Agent, or Firm* — Swanson & Bratschun, L.L.C.

(57) ABSTRACT

The present invention relates to the delivery of antipsychotics through an inhalation route. Specifically, it relates to aerosols containing antipsychotics that are used in inhalation therapy. In a method aspect of the present invention, an antipsychotic is delivered to a patient through an inhalation route. The method comprises: a) heating a composition, wherein the composition comprises an antipsychotic, to form a vapor; and, b) allowing the vapor to cool, thereby forming a condensation aerosol comprising particles with less than 5% antipsychotic drug degradation products. In a kit aspect of the present invention, a kit for delivering an antipsychotic through an inhalation route is provided which comprises: a) a thin coating of an antipsychotic composition and b) a device for dispensing said thin coating as a condensation aerosol.

8 Claims, 1 Drawing Sheet

U.S. PATENT DOCUMENTS

| | | |
|---|---|---|
| 5,605,146 A | 2/1997 | Sarela |
| 5,649,554 A | 7/1997 | Sprinkel |
| 5,666,977 A | 9/1997 | Higgins et al. |
| 5,694,919 A | 12/1997 | Rubsamen et al. |
| 5,735,263 A | 4/1998 | Rubsamen et al. |
| 5,738,865 A | 4/1998 | Baichwal et al. |
| 5,743,251 A | 4/1998 | Howell et al. |
| 5,758,637 A | 6/1998 | Ivri et al. |
| 5,767,117 A | 6/1998 | Moskowitz et al. |
| 5,819,756 A | 10/1998 | Mielordt |
| 5,840,246 A | 11/1998 | Hammons et al. |
| 5,855,913 A | 1/1999 | Hanes et al. |
| 5,874,481 A | 2/1999 | Weers et al. |
| 5,894,841 A | 4/1999 | Voges |
| 5,915,378 A | 6/1999 | Lloyd et al. |
| 5,918,595 A | 7/1999 | Olsson |
| 5,934,272 A | 8/1999 | Lloyd et al. |
| 5,957,124 A | 9/1999 | Lloyd et al. |
| 5,960,792 A | 10/1999 | Lloyd et al. |
| 5,993,805 A | 11/1999 | Sutton et al. |
| 6,041,777 A | 3/2000 | Faithfull et al. |
| 6,051,566 A | 4/2000 | Bianco |
| 6,090,212 A | 7/2000 | Mahawili |
| 6,095,134 A | 8/2000 | Sievers et al. |
| 6,095,153 A | 8/2000 | Kessler et al. |
| 6,102,036 A | 8/2000 | Slutsky et al. |
| 6,131,570 A | 10/2000 | Schuster et al. |
| 6,136,295 A | 10/2000 | Edwards et al. |
| 6,155,268 A | 12/2000 | Takeuchi |
| 6,158,431 A | 12/2000 | Poole |
| 6,234,167 B1 | 5/2001 | Cox et al. |
| 6,241,969 B1 | 6/2001 | Saidi et al. |
| 6,255,334 B1 | 7/2001 | Sands |
| 6,299,900 B1 | 10/2001 | Reed et al. |
| 6,306,431 B1 | 10/2001 | Zhang et al. |
| 6,376,550 B1 | 4/2002 | Raber et al. |
| 6,420,351 B1 | 7/2002 | Tsai et al. |
| 6,506,762 B1 | 1/2003 | Horvath et al. |
| 6,514,482 B1 | 2/2003 | Bartus et al. |
| 6,591,839 B2 | 7/2003 | Meyer et al. |
| 6,632,047 B2 | 10/2003 | Vinegar et al. |
| 6,682,716 B2 | 1/2004 | Hodges et al. |
| 6,701,922 B2 | 3/2004 | Hindle et al. |
| 6,716,415 B2 | 4/2004 | Rabinowitz et al. |
| 6,716,416 B2 | 4/2004 | Rabinowitz et al. |
| 6,716,417 B2 | 4/2004 | Rabinowitz et al. |
| 6,737,042 B2 | 5/2004 | Rabinowitz et al. |
| 6,737,043 B2 | 5/2004 | Rabinowitz et al. |
| 6,740,307 B2 | 5/2004 | Rabinowitz et al. |
| 6,740,308 B2 | 5/2004 | Rabinowitz et al. |
| 6,740,309 B2 | 5/2004 | Rabinowitz et al. |
| 6,743,415 B2 | 6/2004 | Rabinowitz et al. |
| 6,759,029 B2 | 7/2004 | Hale et al. |
| 6,772,756 B2 | 8/2004 | Shayan |
| 6,776,978 B2 | 8/2004 | Rabinowitz et al. |
| 6,780,399 B2 | 8/2004 | Rabinowitz et al. |
| 6,780,400 B2 | 8/2004 | Rabinowitz et al. |
| 6,783,753 B2 | 8/2004 | Rabinowitz et al. |
| 6,797,259 B2 | 9/2004 | Rabinowitz et al. |
| 6,803,031 B2 | 10/2004 | Rabinowitz et al. |
| 6,805,853 B2 | 10/2004 | Rabinowitz et al. |
| 6,805,854 B2 | 10/2004 | Hale et al. |
| 6,814,954 B2 | 11/2004 | Rabinowitz et al. |
| 6,814,955 B2 | 11/2004 | Rabinowitz et al. |
| 6,855,310 B2 | 2/2005 | Rabinowitz et al. |
| 6,884,408 B2 | 4/2005 | Rabinowitz et al. |
| 6,994,843 B2 | 2/2006 | Rabinowitz et al. |
| 7,005,121 B2 | 2/2006 | Rabinowitz et al. |
| 7,005,122 B2 | 2/2006 | Hale et al. |
| 7,008,615 B2 | 3/2006 | Rabinowitz et al. |
| 7,008,616 B2 | 3/2006 | Rabinowitz et al. |
| 7,011,819 B2 | 3/2006 | Hale et al. |
| 7,014,840 B2 | 3/2006 | Hale et al. |
| 7,014,841 B2 | 3/2006 | Rabinowitz et al. |
| 7,018,619 B2 | 3/2006 | Rabinowitz et al. |
| 7,018,620 B2 | 3/2006 | Rabinowitz et al. |
| 7,018,621 B2 | 3/2006 | Hale et al. |
| 7,022,312 B2 | 4/2006 | Rabinowitz et al. |
| 7,029,658 B2 | 4/2006 | Rabinowitz et al. |
| 7,033,575 B2 | 4/2006 | Rabinowitz et al. |
| 7,045,118 B2 | 5/2006 | Rabinowitz et al. |
| 7,045,119 B2 | 5/2006 | Rabinowitz et al. |
| 7,048,909 B2 | 5/2006 | Rabinowitz et al. |
| 7,052,679 B2 | 5/2006 | Rabinowitz et al. |
| 7,052,680 B2 | 5/2006 | Rabinowitz et al. |
| 7,060,254 B2 | 6/2006 | Rabinowitz et al. |
| 7,060,255 B2 | 6/2006 | Rabinowitz et al. |
| 7,063,830 B2 | 6/2006 | Rabinowitz et al. |
| 7,063,831 B2 | 6/2006 | Rabinowitz et al. |
| 7,063,832 B2 | 6/2006 | Rabinowitz et al. |
| 7,067,114 B2 | 6/2006 | Rabinowitz et al. |
| 7,070,761 B2 | 7/2006 | Rabinowitz et al. |
| 7,070,762 B2 | 7/2006 | Rabinowitz et al. |
| 7,070,763 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,070,766 B2 | 7/2006 | Rabinowitz et al. |
| 7,078,016 B2 | 7/2006 | Rabinowitz et al. |
| 7,078,017 B2 | 7/2006 | Rabinowitz et al. |
| 7,078,018 B2 | 7/2006 | Rabinowitz et al. |
| 7,078,019 B2 | 7/2006 | Rabinowitz et al. |
| 7,078,020 B2 | 7/2006 | Rabinowitz et al. |
| 7,087,216 B2 | 8/2006 | Rabinowitz et al. |
| 7,087,217 B2 | 8/2006 | Rabinowitz et al. |
| 7,087,218 B2 | 8/2006 | Rabinowitz et al. |
| 7,090,830 B2 | 8/2006 | Hale et al. |
| 7,094,392 B2 | 8/2006 | Rabinowitz et al. |
| 7,108,847 B2 | 9/2006 | Rabinowitz et al. |
| 7,115,250 B2 | 10/2006 | Rabinowitz et al. |
| 7,169,378 B2 | 1/2007 | Rabinowitz et al. |
| 7,402,777 B2 | 7/2008 | Ron et al. |
| 7,442,368 B2 | 10/2008 | Rabinowitz et al. |
| 7,445,768 B2 | 11/2008 | Rabinowitz et al. |
| 7,449,172 B2 | 11/2008 | Rabinowitz et al. |
| 7,449,173 B2 | 11/2008 | Rabinowitz et al. |
| 7,449,174 B2 | 11/2008 | Rabinowitz et al. |
| 7,449,175 B2 | 11/2008 | Rabinowitz et al. |
| 7,458,374 B2 | 12/2008 | Hale et al. |
| 7,465,435 B2 | 12/2008 | Rabinowitz et al. |
| 7,465,436 B2 | 12/2008 | Rabinowitz et al. |
| 7,465,437 B2 | 12/2008 | Rabinowitz et al. |
| 7,468,179 B2 | 12/2008 | Rabinowitz et al. |
| 7,470,421 B2 | 12/2008 | Rabinowitz et al. |
| 7,485,285 B2 | 2/2009 | Rabinowitz et al. |
| 7,488,469 B2 | 2/2009 | Rabinowitz et al. |
| 7,491,047 B2 | 2/2009 | Rabinowitz et al. |
| 7,498,019 B2 | 3/2009 | Hale et al. |
| 7,507,397 B2 | 3/2009 | Rabinowitz et al. |
| 7,507,398 B2 | 3/2009 | Rabinowitz et al. |
| 7,510,702 B2 | 3/2009 | Rabinowitz et al. |
| 7,524,484 B2 | 4/2009 | Rabinowitz et al. |
| 7,537,009 B2 | 5/2009 | Hale et al. |
| 7,540,286 B2 | 6/2009 | Cross et al. |
| 7,550,133 B2 | 6/2009 | Hale et al. |
| 7,585,493 B2 * | 9/2009 | Hale et al. ............ 424/45 |
| 7,601,337 B2 * | 10/2009 | Rabinowitz et al. ............ 424/45 |
| 2001/0020147 A1 | 9/2001 | Staniforth et al. |
| 2002/0031480 A1 | 3/2002 | Peart et al. |
| 2002/0037828 A1 | 3/2002 | Wilson et al. |
| 2002/0058009 A1 | 5/2002 | Bartus et al. |
| 2002/0086852 A1 | 7/2002 | Cantor |
| 2002/0112723 A1 | 8/2002 | Schuster et al. |
| 2002/0117175 A1 | 8/2002 | Kottayil et al. |
| 2002/0176841 A1 | 11/2002 | Barker et al. |
| 2003/0004142 A1 | 1/2003 | Prior et al. |
| 2003/0015196 A1 | 1/2003 | Hodges et al. |
| 2003/0032638 A1 | 2/2003 | Kim et al. |
| 2003/0051728 A1 | 3/2003 | Lloyd et al. |
| 2003/0062042 A1 | 4/2003 | Wensley et al. |
| 2003/0118512 A1 | 6/2003 | Shen |
| 2003/0131843 A1 | 7/2003 | Lu |
| 2003/0138508 A1 | 7/2003 | Novack et al. |
| 2004/0009128 A1 | 1/2004 | Rabinowitz et al. |
| 2004/0016427 A1 | 1/2004 | Byron et al. |
| 2004/0096402 A1 | 5/2004 | Hodges et al. |
| 2004/0099266 A1 | 5/2004 | Cross et al. |

| | | | |
|---|---|---|---|
| 2004/0101481 | A1 | 5/2004 | Hale et al. |
| 2004/0102434 | A1 | 5/2004 | Hale et al. |
| 2004/0105818 | A1 | 6/2004 | Every et al. |
| 2004/0234699 | A1 | 11/2004 | Hale et al. |
| 2004/0234914 | A1 | 11/2004 | Hale et al. |
| 2004/0234916 | A1 | 11/2004 | Hale et al. |
| 2005/0034723 | A1 | 2/2005 | Bennett et al. |
| 2005/0037506 | A1 | 2/2005 | Hale et al. |
| 2005/0079166 | A1 | 4/2005 | Damani et al. |
| 2005/0126562 | A1 | 6/2005 | Rabinowitz et al. |
| 2005/0131739 | A1 | 6/2005 | Rabinowitz et al. |
| 2005/0268911 | A1 | 12/2005 | Cross et al. |
| 2006/0032496 | A1 | 2/2006 | Hale et al. |
| 2006/0032501 | A1 | 2/2006 | Hale et al. |
| 2006/0120962 | A1 | 6/2006 | Rabinowitz et al. |
| 2006/0193788 | A1 | 8/2006 | Hale et al. |
| 2006/0257329 | A1 | 11/2006 | Rabinowitz et al. |
| 2006/0280692 | A1 | 12/2006 | Rabinowitz et al. |
| 2007/0028916 | A1 | 2/2007 | Hale et al. |
| 2007/0031340 | A1 | 2/2007 | Hale et al. |
| 2007/0122353 | A1 | 5/2007 | Hale et al. |
| 2007/0140982 | A1 | 6/2007 | Every et al. |
| 2007/0286816 | A1 | 12/2007 | Hale et al. |
| 2008/0110872 | A1 | 5/2008 | Hale et al. |
| 2008/0175796 | A1 | 7/2008 | Rabinowitz et al. |
| 2008/0216828 | A1 | 9/2008 | Wensley |
| 2008/0299048 | A1 | 12/2008 | Hale et al. |
| 2008/0306285 | A1 | 12/2008 | Hale et al. |
| 2008/0311176 | A1 | 12/2008 | Hale et al. |
| 2009/0062254 | A1 | 3/2009 | Hale et al. |
| 2009/0071477 | A1 | 3/2009 | Hale et al. |

FOREIGN PATENT DOCUMENTS

| | | |
|---|---|---|
| EP | 0 606 486 | 7/1994 |
| EP | 1 080 720 | 3/2001 |
| GB | 502 761 | 1/1938 |
| WO | WO 94/09842 | 5/1994 |
| WO | WO 96/09846 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 97/27804 | 8/1997 |
| WO | WO 97/35562 | 10/1997 |
| WO | WO 97/36574 | 10/1997 |
| WO | WO 98/02186 | 1/1998 |
| WO | WO 98/22170 | 5/1998 |
| WO | WO 98/31346 | 7/1998 |
| WO | WO 98/36651 | 8/1998 |
| WO | WO 98/37896 | 8/1998 |
| WO | WO 99/16419 | 4/1999 |
| WO | WO 99/64094 | 12/1999 |
| WO | WO 00/00176 | 1/2000 |
| WO | WO 00/00215 | 1/2000 |
| WO | WO 00/27359 | 5/2000 |
| WO | WO 00/27363 | 5/2000 |
| WO | WO 00/29053 | 5/2000 |
| WO | WO 00/47203 | 9/2000 |
| WO | WO 00/64940 | 11/2000 |
| WO | WO 00/66084 | 11/2000 |
| WO | WO 00/66206 | 11/2000 |
| WO | WO 00/76673 | 12/2000 |
| WO | WO 01/05459 | 1/2001 |
| WO | WO 01/12174 | 2/2001 |
| WO | WO 01/13957 | 3/2001 |
| WO | WO 01/32144 | 5/2001 |
| WO | WO 01/41732 | 6/2001 |
| WO | WO 01/95903 | 12/2001 |
| WO | WO 02/00198 | 1/2002 |
| WO | WO 02/24158 | 3/2002 |
| WO | WO 03/037412 | 5/2003 |

OTHER PUBLICATIONS

Office Action mailed Dec. 4, 2003 with respect to U.S. Appl. No. 10/057,198.
Office Action mailed Sep. 20, 2005 with respect to U.S. Appl. No. 10/057,198.
Office Action mailed Jan. 12, 2005 with respect to U.S. Appl. No. 10/057,197.
Office Action mailed Jun. 3, 2004 with respect to U.S. Appl. No. 10/057,197.
Office Action mailed Dec. 15, 2003 with respect to U.S. Appl. No. 10/057,197.
Office Action mailed Sep. 21, 2006 with respect to U.S. Appl. No. 10/057,197.
Office Action mailed Feb. 27, 2004 with respect to U.S. Appl. No. 10/146,080.
Office Action mailed Mar. 20, 2007 with respect to U.S. Appl. No. 10/146,080.
Office Action mailed Jun. 5, 2006 with respect to U.S. Appl. No. 10/146,080.
Office Action mailed Aug. 25, 2005 with respect to U.S. Appl. No. 10/146,080.
Office Action mailed Aug. 13, 2003 with respect to U.S. Appl. No. 10/153,313.
Bennett, R. L. et al. (1981). "Patient-Controlled Analgesia: A New Concept of Postoperative Pain Relief," Annual Surg. 195(6):700-705.
Carroll, M.E. et al. (1990), "Cocaine-Base Smoking in Rhesus Monkey: Reinforcing and Physiological Effects," Psychopharmacology (Berl) 102:443-450.
Clark, A. and Byron, P. (1986). "Dependence of Pulmonary Absorption Kinetics on Aerosol Particle Size," Z. Erkrank. 166:13-24.
Darquenne, C. et al. (1997). "Aerosol Dispersion in Human Lung: Comparison Between Numerical Simulations and Experiments for Bolus Tests," American Physiological Society. 966-974.
Davies, C.N. et al. (May 1972). "Breathing of Half-Micron Aerosols," Journal of Applied Physiology. 32(5):591-600.
Dershwitz, M., M.D., et al. (Sep. 2000). "Pharmacokinetics and Pharmacodynamics of Inhaled versus Intravenous Morphine in Healthy Volunteers," Anesthesiology. 93(3): 619-628.
Finlay, W.H. (2001). "The Mechanics of Inhaled Pharmaceutical Aerosols", Academic Press: San Diego Formula 2.39. pp. 3-14 (Table of Contents). pp. v-viii.
Gonda,I. (1991). "Particle Deposition in the Human Respiratory Tract," Chapter 176, The Lung: Scientific Foundations. Crystal R.G. and West, J.B. (eds.), Raven Publishers, New York. pp. 2289-2294.
Hatsukami D, et al. (May 1990) "A method for delivery of precise doses of smoked cocaine-base to humans." Pharmacology Biochemistry & Behavior. 36(1):1-7.
Heyder, J. et al. (1986). "Deposition of Particles in the Human Respiratory Tract in the Size Range 0.005-15 .mu.m," J. Aerosol Sci. 17(5):811-822.
Huizer, H., "Analytical studies on illicit heron. V. Efficacy of volatilization during heroin smoking." Pharmaceutisch Weekblad Scientific Edition (1987). 9(4):203-211.
Hurt, R.D., MD and Robertson, C.R., PhD, (Oct. 1998). "Prying Open the Door to the Tobacco Industry's Secrets About Nicotine: The Minnesota Tobacco Trial," JAMA 280(13):1173-1181.
Lichtman, A.H. et al. (1996). "Inhalation Exposure to Volatilized Opioids Produces Antinociception in Mice," Journal of Pharmacology and Experimental Therapeutics. 279(1):69-76.
Martin, B.R. and Lue, L.P. (May/Jun. 1989). "Pyrolysis and Volatilization of Cocaine," Journal of Analytical Toxicology 13:158-162.
Mattox, A.J. and Carroll, M.E., (1996). "Smoked heroin self-administration in rhesus monkeys," Psychopharmacology, 125:195-201.
Meng, Y. et al. "Inhalation Studies With Drugs of Abuse," NIDA Research Monograph, (1997) 173:201-224.
Meng, Y., et al. (1999). "Pharmacological effects of methamphetamine and other stimulants via inhalation exposure," Drug and Alcohol Dependence. 53:111-120.
Pankow, J. (Mar. 2000). ACS Conference—San Francisco—Mar. 26, 2000. Chemistry of Tobacco Smoke. pp. 1-8.
Pankow, J.F. et al. (1997). "Conversion of Nicotine in Tobacco Smoke to Its Volatile and Available Free-Base Form Through the Action of Gaseous Ammonia," Envron. Sci. Technol. 31:2428-2433.

Seeman, J. et al. (1999). "The Form of Nicotine in Tobacco. Thermal Transfer of Nicotine and Nicotine Acid Salts to Nicotine in the Gas Phase," J. Agric. Food Chem. 47(12):5133-5145.

Sekine, H. and Nakahara, Y. (1987). "Abuse of Smoking Methamphetamine Mixed with Tobacco: 1. Inhalation Efficiency and Pyrolysis Products of Methamphetamine," Journal of Forensic Science 32(5):1271-1280.

Vapotronics, Inc. (1998) located at http://www.vapotronics.com.au/banner.htm., 11 pages, (visited on Jun. 5, 2000).

Ward, M.E. MD, et al. (Dec. 1997). "Morphine Pharmacokinetics after Pulmonary Administration from a Novel Aerosol Delivery System," Clinical Pharmacology & Therapeutics 62(6):596-609.

Wood, R.W. et al. (1996). "Generation of Stable Test Atmospheres of Cocaine Base and Its Pyrolyzate, Methylecgonidine, and Demonstration of Their Biological Activity." Pharmacology Biochemistry & Behavior. 55(2):237-248.

Wood, R.W. et al. (1996). "Methylecgonidine Coats the Crack Particle" Pharmacology Biochemistry & Behavior. 53(1):57-66.

Yokochi, Akira, (1991) "Various Particle Generation Method for Inhalation and Characteristecs Thereof", NIRS-M (National Inst. Of Radiological Sciences) 1:3-12 (this ref not listed on non-delivery chart).

* cited by examiner

DELIVERY OF ANTIPSYCHOTICS THROUGH AN INHALATION ROUTE

This application is a continuation of U.S. patent application Ser. No. 11/488,932, filed Jul. 18, 2006, entitled "Delivery of Antipsychotics Through an Inhalation Route," which is a continuation of U.S. Pat. No. 7,078,020 entitled "Delivery of Antipsychotics Through an Inhalation Route," filed Dec. 30, 2003, which is a continuation of U.S. Pat. No. 6,716,416 entitled "Delivery of Antipsychotics Through an Inhalation Route," filed May 20, 2002, which claims priority to U.S. provisional application Ser. No. 60/294,203 entitled "Thermal Vapor Delivery of Drugs," filed May 24, 2001; the entire disclosures of which are hereby incorporated by reference. This application further claims priority to U.S. provisional application Ser. No. 60/317,479 entitled "Aerosol Drug Delivery," filed Sep. 5, 2001, the entire disclosures of which are hereby incorporated by reference. Any disclaimer that may have occurred during the prosecution of the above-referenced applications is hereby expressly rescinded, and reconsideration of all relevant art is respectfully requested.

FIELD OF THE INVENTION

The present invention relates to the delivery of antipsychotics through an inhalation route. Specifically, it relates to aerosols containing antipsychotics that are used in inhalation therapy.

BACKGROUND OF THE INVENTION

There are a number of compositions currently marketed for the treatment of psychosis. The compositions contain at least one active ingredient that provides for observed therapeutic effects. Among the active ingredients given in antipsychotic compositions are olanzapine, trifluoperazine, haloperidol, loxapine, risperidone, clozapine, quetiapine, promazine, thiothixene, chlorpromazine, droperidol, prochlorperazine, and fluphenazine.

It is desirable to provide a new route of administration for antipsychotics that rapidly produces peak plasma concentrations of active compound. The provision of such a route is an object of the present invention.

SUMMARY OF THE INVENTION

The present invention relates to the delivery of antipsychotics through an inhalation route. Specifically, it relates to aerosols containing antipsychotics that are used in inhalation therapy.

In a composition aspect of the present invention, the aerosol comprises particles comprising at least 5 percent by weight of an antipsychotic. Preferably, the particles comprise at least 10 percent by weight of an antipsychotic. More preferably, the particles comprise at least 20 percent, 30 percent, 40 percent, 50 percent, 60 percent, 70 percent, 80 percent, 90 percent, 95 percent, 97 percent, 99 percent, 99.5 percent or 99.97 percent by weight of an antipsychotic.

Typically, the aerosol has a mass of at least 10 µg. Preferably, the aerosol has a mass of at least 100 µg. More preferably, the aerosol has a mass of at least 200 µg.

Typically, the particles comprise less than 10 percent by weight of antipsychotic degradation products. Preferably, the particles comprise less than 5 percent by weight of antipsychotic degradation products. More preferably, the particles comprise less than 2.5, 1, 0.5, 0.1 or 0.03 percent by weight of antipsychotic degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, the aerosol particles have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.5. More preferably, the geometric standard deviation is less than 2.1.

Typically, the aerosol is formed by heating a composition containing an antipsychotic to form a vapor and subsequently allowing the vapor to condense into an aerosol.

Typically, the antipsychotic is a typical antipsychotic or an atypical antipsychotic.

In another composition aspect of the present invention, the aerosol comprises particles comprising at least 5 percent by weight of olanzapine, trifluoperazine, haloperidol, loxapine, risperidone, clozapine, quetiapine, promazine, thiothixene, chlorpromazine, droperidol, prochlorperazine, or fluphenazine. Preferably, the particles comprise at least 10 percent by weight of olanzapine, trifluoperazine, haloperidol, loxapine, risperidone, clozapine, quetiapine, promazine, thiothixene, chlorpromazine, droperidol, prochlorperazine, or fluphenazine. More preferably, the particles comprise at least 20 percent, 30 percent, 40 percent, 50 percent, 60 percent, 70 percent, 80 percent, 90 percent, 95 percent, 97 percent, 99 percent, 99.5 percent or 99.97 percent by weight of olanzapine, trifluoperazine, haloperidol, loxapine, risperidone, clozapine, quetiapine, promazine, thiothixene, chlorpromazine, droperidol, prochlorperazine, or fluphenazine.

Typically, the aerosol has a mass of at least 10 µg. Preferably, the aerosol has a mass of at least 100 µg. More preferably, the aerosol has a mass of at least 200 µg.

Typically, the particles comprise less than 10 percent by weight of olanzapine, trifluoperazine, haloperidol, loxapine, risperidone, clozapine, quetiapine, promazine, thiothixene, chlorpromazine, droperidol, prochlorperazine, or fluphenazine degradation products. Preferably, the particles comprise less than 5 percent by weight of olanzapine, trifluoperazine, haloperidol, loxapine, risperidone, clozapine, quetiapine, promazine, thiothixene, chlorpromazine, droperidol, prochlorperazine, or fluphenazine degradation products. More preferably, the particles comprise less than 2.5, 1, 0.5, 0.1 or 0.03 percent by weight of olanzapine, trifluoperazine, haloperidol, loxapine, risperidone, clozapine, quetiapine, promazine, thiothixene, chlorpromazine, droperidol, prochlorperazine, or fluphenazine degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, where the aerosol comprises olanzapine, the aerosol has an inhalable aerosol drug mass density of between 0.2 mg/L and 20 mg/L. Preferably, the aerosol has an inhalable aerosol drug mass density of between 0.5 mg/L and 10 mg/L. More preferably, the aerosol has an inhalable aerosol drug mass density of between 1 mg/L and 5 mg/L.

Typically, where the aerosol comprises trifluoperazine, the aerosol has an inhalable aerosol drug mass density of between 0.2 mg/L and 10 mg/L. Preferably, the aerosol has an inhalable aerosol drug mass density of between 0.5 mg/L and 8 mg/L. More preferably, the aerosol has an inhalable aerosol drug mass density of between 1 mg/L and 5 mg/L.

Typically, where the aerosol comprises haloperidol, the aerosol has an inhalable aerosol drug mass density of between 0.2 mg/L and 10 mg/L. Preferably, the aerosol has an inhalable aerosol drug mass density of between 0.5 mg/L and 8 mg/L. More preferably, the aerosol has an inhalable aerosol drug mass density of between 1 mg/L and 5 mg/L.

Typically, where the aerosol comprises loxapine, the aerosol has an inhalable aerosol drug mass density of between 2 mg/L and 100 mg/L. Preferably, the aerosol has an inhalable aerosol drug mass density of between 5 mg/L and 80 mg/L. More preferably, the aerosol has an inhalable aerosol drug mass density of between 10 mg/L and 50 mg/L.

Typically, where the aerosol comprises risperidone, the aerosol has an inhalable aerosol drug mass density of between 0.1 mg/L and 5 mg/L. Preferably, the aerosol has an inhalable aerosol drug mass density of between 0.2 mg/L and 3 mg/L. More preferably, the aerosol has an inhalable aerosol drug mass density of between 0.4 mg/L and 2 mg/L.

Typically, where the aerosol comprises clozapine, the aerosol has an inhalable aerosol drug mass density of between 2 mg/L and 200 mg/L. Preferably, the aerosol has an inhalable aerosol drug mass density of between 4 mg/L and 150 mg/L. More preferably, the aerosol has an inhalable aerosol drug mass density of between 10 mg/L and 100 mg/L.

Typically, where the aerosol comprises quetiapine, the aerosol has an inhalable aerosol drug mass density of between 2 mg/L and 200 mg/L. Preferably, the aerosol has an inhalable aerosol drug mass density of between 4 mg/L and 150 mg/L. More preferably, the aerosol has an inhalable aerosol drug mass density of between 10 mg/L and 100 mg/L.

Typically, where the aerosol comprises promazine, the aerosol has an inhalable aerosol drug mass density of between 2 mg/L and 200 mg/L. Preferably, the aerosol has an inhalable aerosol drug mass density of between 4 mg/L and 150 mg/L. More preferably, the aerosol has an inhalable aerosol drug mass density of between 10 mg/L and 100 mg/L.

Typically, where the aerosol comprises thiothixene, the aerosol has an inhalable aerosol drug mass density of between 0.5 mg/L and 20 mg/L. Preferably, the aerosol has an inhalable aerosol drug mass density of between 1 mg/L and 10 mg/L. More preferably, the aerosol has an inhalable aerosol drug mass density of between 2 mg/L and 8 mg/L.

Typically, where the aerosol comprises chlorpromazine, the aerosol has an inhalable aerosol drug mass density of between 2 mg/L and 200 mg/L. Preferably, the aerosol has an inhalable aerosol drug mass density of between 4 mg/L and 150 mg/L. More preferably, the aerosol has an inhalable aerosol drug mass density of between 5 mg/L and 100 mg/L.

Typically, where the aerosol comprises droperidol, the aerosol has an inhalable aerosol drug mass density of between 0.2 mg/L and 20 mg/L. Preferably, the aerosol has an inhalable aerosol drug mass density of between 0.5 mg/L and 10 mg/L. More preferably, the aerosol has an inhalable aerosol drug mass density of between 1 mg/L and 5 mg/L.

Typically, where the aerosol comprises prochlorperazine, the aerosol has an inhalable aerosol drug mass density of between 0.5 mg/L and 20 mg/L. Preferably, the aerosol has an inhalable aerosol drug mass density of between 1 mg/L and 15 mg/L. More preferably, the aerosol has an inhalable aerosol drug mass density of between 2 mg/L and 10 mg/L.

Typically, where the aerosol comprises fluphenazine, the aerosol has an inhalable aerosol drug mass density of between 0.1 mg/L and 10 mg/L. Preferably, the aerosol has an inhalable aerosol drug mass density of between 0.2 mg/L and 8 mg/L. More preferably, the aerosol has an inhalable aerosol drug mass density of between 0.5 mg/L and 5 mg/L.

Typically, the aerosol has an inhalable aerosol particle density greater than $10^6$ particles/mL. Preferably, the aerosol has an inhalable aerosol particle density greater than $10^7$ particles/mL or $10^8$ particles/mL.

Typically, the aerosol particles have a mass median aerodynamic diameter of less than 5 microns, e.g., 0.2 to 3 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.5. More preferably, the geometric standard deviation is less than 2.1.

Typically, the aerosol is formed by heating a composition containing olanzapine, trifluoperazine, haloperidol, loxapine, risperidone, clozapine, quetiapine, promazine, thiothixene, chlorpromazine, droperidol, prochlorperazine, or fluphenazine to form a vapor and subsequently allowing the vapor to condense into an aerosol.

In a method aspect of the present invention, an antipsychotic is delivered to a mammal through an inhalation route. The method comprises: a) heating a composition, wherein the composition comprises at least 5 percent by weight of an antipsychotic, to form a vapor; and, b) allowing the vapor to cool, thereby forming a condensation aerosol comprising particles, which is inhaled by the mammal. Preferably, the composition that is heated comprises at least 10 percent by weight of an antipsychotic. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of an antipsychotic.

Typically, the particles comprise at least 5 percent by weight of an antipsychotic. Preferably, the particles comprise at least 10 percent by weight of an antipsychotic. More preferably, the particles comprise at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of an antipsychotic.

Typically, the condensation aerosol has a mass of at least 10 µg. Preferably, the aerosol has a mass of at least 100 µg. More preferably, the aerosol has a mass of at least 200 µg.

Typically, the particles comprise less than 10 percent by weight of antipsychotic degradation products. Preferably, the particles comprise less than 5 percent by weight of antipsychotic degradation products. More preferably, the particles comprise 2.5, 1, 0.5, 0.1 or 0.03 percent by weight of antipsychotic degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, the particles of the delivered condensation aerosol have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.5. More preferably, the geometric standard deviation is less than 2.1.

Typically, the rate of inhalable aerosol particle formation of the delivered condensation aerosol is greater than 108 particles per second. Preferably, the aerosol is formed at a rate greater than 109 inhalable particles per second. More preferably, the aerosol is formed at a rate greater than 1010 inhalable particles per second.

Typically, the delivered condensation aerosol is formed at a rate greater than 0.5 mg/second. Preferably, the aerosol is formed at a rate greater than 0.75 mg/second. More preferably, the aerosol is formed at a rate greater than 1 mg/second, 1.5 mg/second or 2 mg/second.

Typically, the delivered condensation aerosol results in a peak plasma concentration of an antipsychotic in the mammal in less than 1 h. Preferably, the peak plasma concentration is reached in less than 0.5 h. More preferably, the peak plasma concentration is reached in less than 0.2, 0.1, 0.05, 0.02, 0.01, or 0.005 h (arterial measurement).

Typically, the antipsychotic is a typical antipsychotic or an atypical antipsychotic.

In another method aspect of the present invention, one of olanzapine, trifluoperazine, haloperidol, loxapine, risperidone, clozapine, quetiapine, promazine, thiothixene, chlorpromazine, droperidol, prochlorperazine, or fluphenazine is delivered to a mammal through an inhalation route. The method comprises: a) heating a composition, wherein the composition comprises at least 5 percent by weight of olanzapine, trifluoperazine, haloperidol, loxapine, risperidone, clozapine, quetiapine, promazine, thiothixene, chlorpromazine, droperidol, prochlorperazine, or fluphenazine, to form a vapor; and, b) allowing the vapor to cool, thereby forming a condensation aerosol comprising particles, which is inhaled by the mammal. Preferably, the composition that is heated comprises at least 10 percent by weight of olanzapine, trifluoperazine, haloperidol, loxapine, risperidone, clozapine, quetiapine, promazine, thiothixene, chlorpromazine, droperidol, prochlorperazine, or fluphenazine. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of olanzapine, trifluoperazine, haloperidol, loxapine, risperidone, clozapine, quetiapine, promazine, thiothixene, chlorpromazine, droperidol, prochlorperazine, or fluphenazine.

Typically, the particles comprise at least 5 percent by weight of olanzapine, trifluoperazine, haloperidol, loxapine, risperidone, clozapine, quetiapine, promazine, thiothixene, chlorpromazine, droperidol, prochlorperazine, or fluphenazine. Preferably, the particles comprise at least 10 percent by weight of olanzapine, trifluoperazine, haloperidol, loxapine, risperidone, clozapine, quetiapine, promazine, thiothixene, chlorpromazine, droperidol, prochlorperazine, or fluphenazine. More preferably, the particles comprise at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of olanzapine, trifluoperazine, haloperidol, loxapine, risperidone, clozapine, quetiapine, promazine, thiothixene, chlorpromazine, droperidol, prochlorperazine, or fluphenazine.

Typically, the condensation aerosol has a mass of at least 10 µg. Preferably, the aerosol has a mass of at least 100 µg. More preferably, the aerosol has a mass of at least 200 µg.

Typically, the particles comprise less than 10 percent by weight of olanzapine, trifluoperazine, haloperidol, loxapine, risperidone, clozapine, quetiapine, promazine, thiothixene, chlorpromazine, droperidol, prochlorperazine, or fluphenazine degradation products. Preferably, the particles comprise less than 5 percent by weight of olanzapine, trifluoperazine, haloperidol, loxapine, risperidone, clozapine, quetiapine, promazine, thiothixene, chlorpromazine, droperidol, prochlorperazine, or fluphenazine degradation products. More preferably, the particles comprise 2.5, 1, 0.5, 0.1 or 0.03 percent by weight of olanzapine, trifluoperazine, haloperidol, loxapine, risperidone, clozapine, quetiapine, promazine, thiothixene, chlorpromazine, droperidol, prochlorperazine, or fluphenazine degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, the particles of the delivered condensation aerosol have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.0. Preferably, the geometric standard deviation is less than 2.5. More preferably, the geometric standard deviation is less than 2.1.

Typically, where the aerosol comprises olanzapine, the delivered aerosol has an inhalable aerosol drug mass density of between 0.2 mg/L and 20 mg/L. Preferably, the aerosol has an inhalable aerosol drug mass density of between 0.5 mg/L and 10 mg/L. More preferably, the aerosol has an inhalable aerosol drug mass density of between 1 mg/L and 5 mg/L.

Typically, where the aerosol comprises trifluoperazine, the delivered aerosol has an inhalable aerosol drug mass density of between 0.2 mg/L and 10 mg/L. Preferably, the aerosol has an inhalable aerosol drug mass density of between 0.5 mg/L and 8 mg/L. More preferably, the aerosol has an inhalable aerosol drug mass density of between 1 mg/L and 5 mg/L.

Typically, where the aerosol comprises haloperidol, the delivered aerosol has an inhalable aerosol drug mass density of between 0.2 mg/L and 10 mg/L. Preferably, the aerosol has an inhalable aerosol drug mass density of between 0.5 mg/L and 8 mg/L. More preferably, the aerosol has an inhalable aerosol drug mass density of between 1 mg/L and 5 mg/L.

Typically, where the aerosol comprises loxapine, the delivered aerosol has an inhalable aerosol drug mass density of between 2 mg/L and 100 mg/L. Preferably, the aerosol has an inhalable aerosol drug mass density of between 5 mg/L and 80 mg/L. More preferably, the aerosol has an inhalable aerosol drug mass density of between 10 mg/L and 50 mg/L.

Typically, where the aerosol comprises risperidone, the delivered aerosol has an inhalable aerosol drug mass density of between 0.1 mg/L and 5 mg/L. Preferably, the aerosol has an inhalable aerosol drug mass density of between 0.2 mg/L and 3 mg/L. More preferably, the aerosol has an inhalable aerosol drug mass density of between 0.4 mg/L and 2 mg/L.

Typically, where the aerosol comprises clozapine, the delivered aerosol has an inhalable aerosol drug mass density of between 2 mg/L and 200 mg/L. Preferably, the aerosol has an inhalable aerosol drug mass density of between 4 mg/L and 150 mg/L. More preferably, the aerosol has an inhalable aerosol drug mass density of between 10 mg/L and 100 mg/L.

Typically, where the aerosol comprises quetiapine, the delivered aerosol has an inhalable aerosol drug mass density of between 2 mg/L and 200 mg/L. Preferably, the aerosol has an inhalable aerosol drug mass density of between 4 mg/L and 150 mg/L. More preferably, the aerosol has an inhalable aerosol drug mass density of between 10 mg/L and 100 mg/L.

Typically, where the aerosol comprises promazine, the delivered aerosol has an inhalable aerosol drug mass density of between 2 mg/L and 200 mg/L. Preferably, the aerosol has an inhalable aerosol drug mass density of between 4 mg/L and 150 mg/L. More preferably, the aerosol has an inhalable aerosol drug mass density of between 10 mg/L and 100 mg/L.

Typically, where the aerosol comprises thiothixene, the delivered aerosol has an inhalable aerosol drug mass density of between 0.5 mg/L and 20 mg/L. Preferably, the aerosol has an inhalable aerosol drug mass density of between 1 mg/L and 10 mg/L. More preferably, the aerosol has an inhalable aerosol drug mass density of between 2 mg/L and 8 mg/L.

Typically, where the aerosol comprises chlorpromazine, the delivered aerosol has an inhalable aerosol drug mass density of between 2 mg/L and 200 mg/L. Preferably, the aerosol has an inhalable aerosol drug mass density of between 4 mg/L and 150 mg/L. More preferably, the aerosol has an inhalable aerosol drug mass density of between 5 mg/L and 100 mg/L.

Typically, where the aerosol comprises droperidol, the delivered aerosol has an inhalable aerosol drug mass density of between 0.2 mg/L and 20 mg/L. Preferably, the aerosol has an inhalable aerosol drug mass density of between 0.5 mg/L and 10 mg/L. More preferably, the aerosol has an inhalable aerosol drug mass density of between 1 mg/L and 5 mg/L.

Typically, where the aerosol comprises prochlorperazine, the delivered aerosol has an inhalable aerosol drug mass density of between 0.5 mg/L and 20 mg/L. Preferably, the aerosol has an inhalable aerosol drug mass density of between 1 mg/L and 15 mg/L. More preferably, the aerosol has an inhalable aerosol drug mass density of between 2 mg/L and 10 mg/L.

Typically, where the aerosol comprises fluphenazine, the delivered aerosol has an inhalable aerosol drug mass density of between 0.1 mg/L and 10 mg/L. Preferably, the aerosol has an inhalable aerosol drug mass density of between 0.2 mg/L and 8 mg/L. More preferably, the aerosol has an inhalable aerosol drug mass density of between 0.5 mg/L and 5 mg/L.

Typically, the delivered aerosol has an inhalable aerosol particle density greater than $10^6$ particles/mL. Preferably, the aerosol has an inhalable aerosol particle density greater than $10^7$ particles/mL or $10^8$ particles/mL.

Typically, the rate of inhalable aerosol particle formation of the delivered condensation aerosol is greater than $10^8$ particles per second. Preferably, the aerosol is formed at a rate greater than $10^9$ inhalable particles per second. More preferably, the aerosol is formed at a rate greater than $10^{10}$ inhalable particles per second.

Typically, the delivered condensation aerosol is formed at a rate greater than 0.5 mg/second. Preferably, the aerosol is formed at a rate greater than 0.75 mg/second. More preferably, the aerosol is formed at a rate greater than 1 mg/second, 1.5 mg/second or 2 mg/second.

Typically, where the condensation aerosol comprises olanzapine, between 0.2 mg and 20 mg of olanzapine are delivered to the mammal in a single inspiration. Preferably, between 0.5 mg and 10 mg of olanzapine are delivered to the mammal in a single inspiration. More preferably, between 1 mg and 5 mg of olanzapine are delivered to the mammal in a single inspiration.

Typically, where the condensation aerosol comprises trifluoperazine, between 0.2 mg and 10 mg of trifluoperazine are delivered to the mammal in a single inspiration. Preferably, between 0.5 mg and 8 mg of trifluoperazine are delivered to the mammal in a single inspiration. More preferably, between 1 mg and 5 mg of trifluoperazine are delivered to the mammal in a single inspiration.

Typically, where the condensation aerosol comprises haloperidol, between 0.2 mg and 10 mg of haloperidol are delivered to the mammal in a single inspiration. Preferably, between 0.5 mg and 8 mg of haloperidol are delivered to the mammal in a single inspiration. More preferably, between 1 mg and 5 mg of haloperidol are delivered to the mammal in a single inspiration.

Typically, where the condensation aerosol comprises loxapine, between 2 mg and 100 mg of loxapine are delivered to the mammal in a single inspiration. Preferably, between 5 mg and 80 mg of loxapine are delivered to the mammal in a single inspiration. More preferably, between 10 mg and 50 mg of loxapine are delivered to the mammal in a single inspiration.

Typically, where the condensation aerosol comprises risperidone, between 0.1 mg and 5 mg of risperidone are delivered to the mammal in a single inspiration. Preferably, between 0.2 mg and 3 mg of risperidone are delivered to the mammal in a single inspiration. More preferably, between 0.4 mg and 2 mg of risperidone are delivered to the mammal in a single inspiration.

Typically, where the condensation aerosol comprises clozapine, between 2 mg and 200 mg of clozapine are delivered to the mammal in a single inspiration. Preferably, between 4 mg and 150 mg of clozapine are delivered to the mammal in a single inspiration. More preferably, between 10 mg and 100 mg of clozapine are delivered to the mammal in a single inspiration.

Typically, where the condensation aerosol comprises quetiapine, between 2 mg and 200 mg of quetiapine are delivered to the mammal in a single inspiration. Preferably, between 4 mg and 150 mg of quetiapine are delivered to the mammal in a single inspiration. More preferably, between 10 mg and 100 mg of quetiapine are delivered to the mammal in a single inspiration.

Typically, where the condensation aerosol comprises promazine, between 2 mg and 200 mg of promazine are delivered to the mammal in a single inspiration. Preferably, between 4 mg and 150 mg of promazine are delivered to the mammal in a single inspiration. More preferably, between 10 mg and 100 mg of promazine are delivered to the mammal in a single inspiration.

Typically, where the condensation aerosol comprises thiothixene, between 0.5 mg and 20 mg of thiothixene are delivered to the mammal in a single inspiration. Preferably, between 1 mg and 10 mg of thiothixene are delivered to the mammal in a single inspiration. More preferably, between 2 mg and 8 mg of thiothixene are delivered to the mammal in a single inspiration.

Typically, where the condensation aerosol comprises chlorpromazine, between 2 mg and 200 mg of chlorpromazine are delivered to the mammal in a single inspiration. Preferably, between 4 mg and 150 mg of chlorpromazine are delivered to the mammal in a single inspiration. More preferably, between 5 mg and 100 mg of chlorpromazine are delivered to the mammal in a single inspiration.

Typically, where the condensation aerosol comprises droperidol, between 0.2 mg and 20 mg of droperidol are delivered to the mammal in a single inspiration. Preferably, between 0.5 mg and 10 mg of droperidol are delivered to the mammal in a single inspiration. More preferably, between 1 mg and 5 mg of droperidol are delivered to the mammal in a single inspiration.

Typically, where the condensation aerosol comprises prochlorperazine, between 0.5 mg and 20 mg of prochlorperazine are delivered to the mammal in a single inspiration. Preferably, between 1 mg and 15 mg of prochlorperazine are delivered to the mammal in a single inspiration. More preferably, between 2 mg and 10 mg of prochlorperazine are delivered to the mammal in a single inspiration.

Typically, where the condensation aerosol comprises fluphenazine, between 0.1 mg and 10 mg of fluphenazine are delivered to the mammal in a single inspiration. Preferably, between 0.2 mg and 8 mg of fluphenazine are delivered to the mammal in a single inspiration. More preferably, between 0.5 mg and 5 mg of fluphenazine are delivered to the mammal in a single inspiration.

Typically, the delivered condensation aerosol results in a peak plasma concentration of olanzapine, trifluoperazine, haloperidol, loxapine, risperidone, clozapine, quetiapine, promazine, thiothixene, chlorpromazine, droperidol, prochlorperazine, or fluphenazine in the mammal in less than 1 h. Preferably, the peak plasma concentration is reached in less than 0.5 h. More preferably, the peak plasma concentration is reached in less than 0.2, 0.1, 0.05, 0.02, 0.01, or 0.005 h (arterial measurement).

Typically, the delivered condensation aerosol is used to treat psychosis.

In a kit aspect of the present invention, a kit for delivering an antipsychotic through an inhalation route to a mammal is provided which comprises: a) a composition comprising at least 5 percent by weight of an antipsychotic; and, b) a device that forms an antipsychotic aerosol from the composition, for inhalation by the mammal. Preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of an antipsychotic.

Typically, the device contained in the kit comprises: a) an element for heating the antipsychotic composition to form a vapor; b) an element allowing the vapor to cool to form an aerosol; and, c) an element permitting the mammal to inhale the aerosol.

In a kit aspect of the present invention, a kit for delivering olanzapine, trifluoperazine, haloperidol, loxapine, risperidone, clozapine, quetiapine, promazine, thiothixene, chlorpromazine, droperidol, prochlorperazine, or fluphenazine through an inhalation route to a mammal is provided which comprises: a) a composition comprising at least 5 percent by weight of olanzapine, trifluoperazine, haloperidol, loxapine, risperidone, clozapine, quetiapine, promazine, thiothixene, chlorpromazine, droperidol, prochlorperazine, or fluphenazine; and, b) a device that forms a olanzapine, trifluoperazine, haloperidol, loxapine, risperidone, clozapine, quetiapine, promazine, thiothixene, chlorpromazine, droperidol, prochlorperazine, or fluphenazine aerosol from the composition, for inhalation by the mammal. Preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of olanzapine, trifluoperazine, haloperidol, loxapine, risperidone, clozapine, quetiapine, promazine, thiothixene, chlorpromazine, droperidol, prochlorperazine, or fluphenazine.

Typically, the device contained in the kit comprises: a) an element for heating the olanzapine, trifluoperazine, haloperidol, loxapine, risperidone, clozapine, quetiapine, promazine, thiothixene, chlorpromazine, droperidol, prochlorperazine, or fluphenazine composition to form a vapor; b) an element allowing the vapor to cool to form an aerosol; and, c) an element permitting the mammal to inhale the aerosol.

DETAILED DESCRIPTION OF THE INVENTION

Definitions

Figure 1:
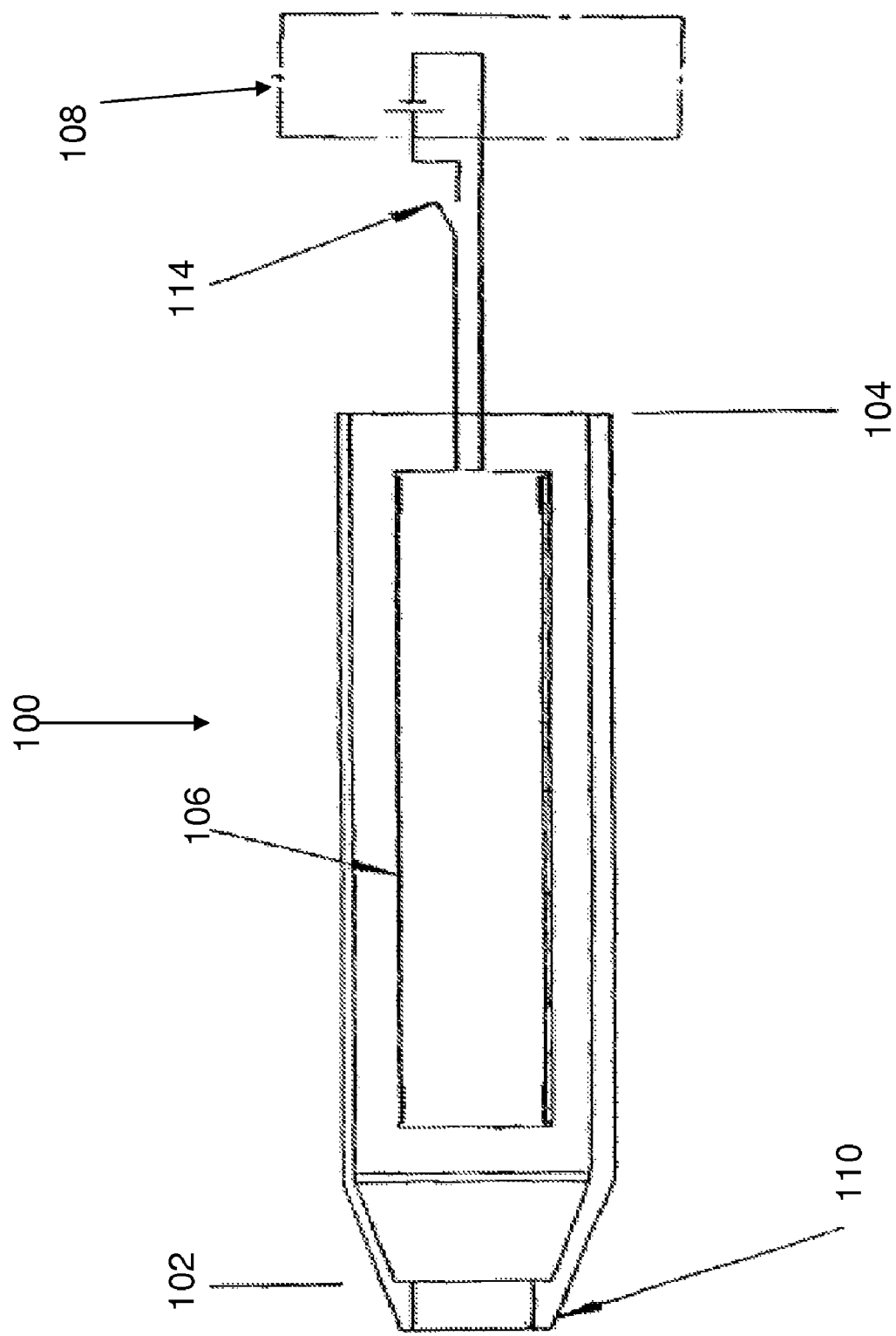
FIG. 1 shows a cross-sectional view of a device used to deliver antipsychotic aerosols to a mammal through an inhalation route.

"Aerodynamic diameter" of a given particle refers to the diameter of a spherical droplet with a density of 1 g/mL (the density of water) that has the same settling velocity as the given particle.

"Aerosol" refers to a suspension of solid or liquid particles in a gas.

"Aerosol drug mass density" refers to the mass of an antipsychotic per unit volume of aerosol.

"Aerosol mass density" refers to the mass of particulate matter per unit volume of aerosol.

"Aerosol particle density" refers to the number of particles per unit volume of aerosol.

"Amorphous particle" refers to a particle that does not contain more than 50 percent by weight of a crystalline form. Preferably, the particle does not contain more than 25 percent by weight of a crystalline form. More preferably, the particle does not contain more than 10 percent by weight of a crystalline form.

"Antipsychotic degradation product" refers to a compound resulting from a chemical modification of an antipsychotic. The modification, for example, can be the result of a thermally or photochemically induced reaction. Such reactions include, without limitation, oxidation and hydrolysis.

"Chlorpromazine" refers to 10-(3-dimethylaminopropyl)-2-chlorphenothiazine.

"Chlorpromazine degradation product" refers to a compound resulting from a chemical modification of chlorpromazine. The modification, for example, can be the result of a thermally or photochemically induced reaction. Such reactions include, without limitation, oxidation and hydrolysis.

"Clozapine" refers to 8-chloro-11-(4-methyl-1-piperazinyl)-5H-dibenzo[b,e]-[1,4]benzodiazepine.

"Clozapine degradation product" refers to a compound resulting from a chemical modification of clozapine. The modification, for example, can be the result of a thermally or photochemically induced reaction. Such reactions include, without limitation, oxidation and hydrolysis. Examples of degradation products include compounds of molecular formula $C_6H_{12}N_2O$ and $C_{13}H_8N_2Cl$.

"Droperidol" refers to 1-[1-[4-(4-fluorophenyl)-4-oxobutyl]-1,2,3,6-tetrahydro-4-pyridinyl]-1,3-dihydro-2H-benzimidazol-2-one.

"Droperidol degradation product" refers to a compound resulting from a chemical modification of droperidol. The modification, for example, can be the result of a thermally or photochemically induced reaction. Such reactions include, without limitation, oxidation and hydrolysis. An example of a degradation product is 2-hydroxy-benzimidazole.

"Condensation aerosol" refers to an aerosol formed by vaporization of a substance followed by condensation of the substance into an aerosol.

"Fluphenazine" refers to 4-[3-[2-(trifluoromethyl)-10H-phenothiazin-10-yl]propyl]-1-piperazine-ethanol.

"Fluphenazine degradation product" refers to a compound resulting from a chemical modification of fluphenazine. The modification, for example, can be the result of a thermally or photochemically induced reaction. Such reactions include, without limitation, oxidation and hydrolysis. Examples of degradation products include $C_{13}H_8NSF_3$ (removal of substituted propyl chain from nitrogen) and $C_{13}H_8NOSF_3$ (oxidation of $C_{13}H_8NSF_3$).

"Haloperidol" refers to 4-[4-(p-chlorophenyl)-4-hydroxypiperidinol]-4'-fluorobutyrophenone.

"Haloperidol degradation product" refers to a compound resulting from a chemical modification of haloperidol. The modification, for example, can be the result of a thermally or photochemically induced reaction. Such reactions include, without limitation, oxidation and hydrolysis. An example of a degradation product is a compound of molecular formula $C_{11}H_{14}NOCl$ (removal of substituted propyl sidechain from nitrogen).

"Inhalable aerosol drug mass density" refers to the aerosol drug mass density produced by an inhalation device and delivered into a typical patient tidal volume.

"Inhalable aerosol mass density" refers to the aerosol mass density produced by an inhalation device and delivered into a typical patient tidal volume.

"Inhalable aerosol particle density" refers to the aerosol particle density of particles of size between 100 nm and 5 microns produced by an inhalation device and delivered into a typical patient tidal volume.

"Loxapine" refers to 2-chloro-11-(4-methyl-1-piperazinyl)-dibenz[b,f]-[1,4]diazepine.

"Loxapine degradation product" refers to a compound resulting from a chemical modification of loxapine. The modification, for example, can be the result of a thermally or photochemically induced reaction. Such reactions include, without limitation, oxidation and hydrolysis.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

"Olanzapine" refers to 2-methyl-4-(4-methyl)-1-piperazinyl)-10H-thieno[2,3-b][1,5]benzodiazepine.

"Olanzapine degradation product" refers to a compound resulting from a chemical modification of olanzapine. The modification, for example, can be the result of a thermally or photochemically induced reaction. Such reactions include, without limitation, oxidation and hydrolysis. Examples of degradation products are $C_{12}H_{10}N_2OS$ (replacement of piperazine group with OH) and $C_5H_{12}N_2$ (1-methylpiperazine).

"Prochlorperazine" refers to 2-chloro-10-[3-(4-methyl-1-piperazinyl)propyl]-10H-phenothiazine.

"Prochlorperazine degradation product" refers to a compound resulting from a chemical modification of prochlorperazine. The modification, for example, can be the result of a thermally or photochemically induced reaction. Such reactions include, without limitation, oxidation and hydrolysis.

"Promazine" refers to N,N-dimethyl-10H-phenothiazine-10-propanamine.

"Promazine degradation product" refers to a compound resulting from a chemical modification of promazine. The modification, for example, can be the result of a thermally or photochemically induced reaction. Such reactions include, without limitation, oxidation and hydrolysis.

"Quetiapine" refers to 2-[2-(4-dibenzo[b,f][1,4]thiazepin-11-yl-1-piperazinyl)-ethoxy]-ethanol.

"Quetiapine degradation product" refers to a compound resulting from a chemical modification of quetiapine. The modification, for example, can be the result of a thermally or photochemically induced reaction. Such reactions include, without limitation, oxidation and hydrolysis.

"Rate of aerosol formation" refers to the mass of aerosolized particulate matter produced by an inhalation device per unit time.

"Rate of inhalable aerosol particle formation" refers to the number of particles of size between 100 nm and 5 microns produced by an inhalation device per unit time.

"Rate of drug aerosol formation" refers to the mass of aerosolized antipsychotic produced by an inhalation device per unit time.

"Risperidone" refers to 3-[2-[4-(6-fluoro-1,2-benzisoxazol-3-yl)-1-piperidinyl]ethyl]6,7,8,9-tetrahydro-2-methyl-4H-pyrido[1,2-a]pyrimidin-4-one.

"Risperidone degradation product" refers to a compound resulting from a chemical modification of risperidone. The modification, for example, can be the result of a thermally or photochemically induced reaction. Such reactions include, without limitation, oxidation and hydrolysis.

"Settling velocity" refers to the terminal velocity of an aerosol particle undergoing gravitational settling in air.

"Thiothixene" refers to cis-9-[3-(4-methyl-1-piperazinyl) propylidene]-2-(dimethylsulfonamido)thioxanthene.

"Thiothixene degradation product" refers to a compound resulting from a chemical modification of thiothixene. The modification, for example, can be the result of a thermally or photochemically induced reaction. Such reactions include, without limitation, oxidation and hydrolysis. An example of a degradation product is a compound of chemical formula $C_{13}H_9NO_4S_2$.

"Trifluoperazine" refers to 2-trifluoro-methyl-10-[3'-(1-methyl-4-piperazinyl)-propyl]phenothiazine.

"Trifluoperazine degradation product" refers to a compound resulting from a chemical modification of trifluoperazine. The modification, for example, can be the result of a thermally or photochemically induced reaction. Such reactions include, without limitation, oxidation and hydrolysis. An example of a degradation product is $C_{11}H_8NSF_3$ (removal of substituted propyl sidechain from nitrogen).

"Typical patient tidal volume" refers to 1 L for an adult patient and 15 mL/kg for a pediatric patient.

"Vapor" refers to a gas, and "vapor phase" refers to a gas phase. The term "thermal vapor" refers to a vapor phase, aerosol, or mixture of aerosol-vapor phases, formed preferably by heating.

Formation of Antipsychotic Containing Aerosols

Any suitable method is used to form the aerosols of the present invention. A preferred method, however, involves heating a composition comprising an antipsychotic to form a vapor, followed by cooling of the vapor such that it condenses to provide an antipsychotic comprising aerosol (condensation aerosol). The composition is heated in one of four forms: as pure active compound (e.g., pure olanzapine, trifluoperazine, haloperidol, loxapine, risperidone, clozapine, quetiapine, promazine, thiothixene, chlorpromazine, droperidol or fluphenazine); as a mixture of active compound and a pharmaceutically acceptable excipient; as a salt form of the pure active compound; and, as a mixture of active compound salt form and a pharmaceutically acceptable excipient.

Salt forms of antipsychotics (e.g., olanzapine, trifluoperazine, haloperidol, loxapine, risperidone, clozapine, quetiapine, promazine, thiothixene, chlorpromazine, droperidol, prochlorperazine or fluphenazine) are either commercially available or are obtained from the corresponding free base using well known methods in the art. A variety of pharmaceutically acceptable salts are suitable for aerosolization. Such salts include, without limitation, the following: hydrochloric acid, hydrobromic acid, acetic acid, maleic acid, formic acid, and fumaric acid salts.

Pharmaceutically acceptable excipients may be volatile or nonvolatile. Volatile excipients, when heated, are concurrently volatilized, aerosolized and inhaled with the antipsychotic. Classes of such excipients are known in the art and include, without limitation, gaseous, supercritical fluid, liquid and solid solvents. The following is a list of exemplary carriers within the classes: water; terpenes, such as menthol; alcohols, such as ethanol, propylene glycol, glycerol and other similar alcohols; dimethylformamide; dimethylacetamide; wax; supercritical carbon dioxide; dry ice; and mixtures thereof.

Solid supports on which the composition is heated are of a variety of shapes. Examples of such shapes include, without limitation, cylinders of less than 1.0 mm in diameter, boxes of less than 1.0 mm thickness and virtually any shape permeated by small (e.g., less than 1.0 mm-sized) pores. Preferably, solid supports provide a large surface to volume ratio (e.g., greater than 100 per meter) and a large surface to mass ratio (e.g., greater than 1 $cm^2$ per gram).

A solid support of one shape can also be transformed into another shape with different properties. For example, a flat sheet of 0.25 mm thickness has a surface to volume ratio of approximately 8,000 per meter. Rolling the sheet into a hollow cylinder of 1 cm diameter produces a support that retains the high surface to mass ratio of the original sheet but has a lower surface to volume ratio (about 400 per meter).

A number of different materials are used to construct the solid supports. Classes of such materials include, without limitation, metals, inorganic materials, carbonaceous materials and polymers. The following are examples of the material classes: aluminum, silver, gold, stainless steel, copper and tungsten; silica, glass, silicon and alumina; graphite, porous carbons, carbon yarns and carbon felts; polytetrafluoroethylene and polyethylene glycol. Combinations of materials and coated variants of materials are used as well.

Where aluminum is used as a solid support, aluminum foil is a suitable material. Examples of silica, alumina and silicon based materials include amphorous silica S-5631 (Sigma, St. Louis, Mo.), BCR171 (an alumina of defined surface area greater than 2 $m^2$/g from Aldrich, St. Louis, Mo.) and a silicon wafer as used in the semiconductor industry. Carbon yarns and felts are available from American Kynol, Inc., New York, N.Y. Chromatography resins such as octadecycl silane chemically bonded to porous silica are exemplary coated variants of silica.

The heating of the antipsychotic compositions is performed using any suitable method. Examples of methods by which heat can be generated include the following: passage of current through an electrical resistance element; absorption of electromagnetic radiation, such as microwave or laser light; and, exothermic chemical reactions, such as exothermic solvation, hydration of pyrophoric materials and oxidation of combustible materials.

Delivery of Antipsychotic Containing Aerosols

Antipsychotic containing aerosols of the present invention are delivered to a mammal using an inhalation device. Where the aerosol is a condensation aerosol, the device has at least three elements: an element for heating an antipsychotic containing composition to form a vapor; an element allowing the vapor to cool, thereby providing a condensation aerosol; and, an element permitting the mammal to inhale the aerosol. Various suitable heating methods are described above. The element that allows cooling is, in it simplest form, an inert passageway linking the heating means to the inhalation means. The element permitting inhalation is an aerosol exit portal that forms a connection between the cooling element and the mammal's respiratory system.

One device used to deliver the antipsychotic containing aerosol is described in reference to FIG. 1. Delivery device 100 has a proximal end 102 and a distal end 104, a heating module 106, a power source 108, and a mouthpiece 110. An antipsychotic composition is deposited on a surface 112 of heating module 106. Upon activation of a user activated switch 114, power source 108 initiates heating of heating module 106 (e.g, through ignition of combustible fuel or passage of current through a resistive heating element). The antipsychotic composition volatilizes due to the heating of heating module 106 and condenses to form a condensation aerosol prior to reaching the mouthpiece 110 at the proximal end of the device 102. Air flow traveling from the device distal end 104 to the mouthpiece 110 carries the condensation aerosol to the mouthpiece 110, where it is inhaled by the mammal.

Devices, if desired, contain a variety of components to facilitate the delivery of antipsychotic containing aerosols. For instance, the device may include any component known in the art to control the timing of drug aerosolization relative to inhalation (e.g., breath-actuation), to provide feedback to patients on the rate and/or volume of inhalation, to prevent excessive use (i.e., "lock-out" feature), to prevent use by unauthorized individuals, and/or to record dosing histories.

Dosage of Antipsychotic Containing Aerosols

The dosage amount of antipsychotic in aerosol form is generally no greater than twice the standard dose of the drug given orally. For instance, olanzapine, trifluoperazine, haloperidol, loxapine, risperidone, clozapine, quetiapine, promazine, thiothixene, chlorpromazine, droperidol, prochlorperazine, or fluphenazine are given at strengths of 10 mg, 7.5 mg to 10 mg, 2 mg, 30 mg to 50 mg, 2 mg to 8 mg, 150 mg, 75 mg, 50 mg to 100 mg, 10 mg, 10 mg to 100 mg, 1 mg, 5 mg, and 1 mg respectively for the treatment of psychosis. As aerosols, 0.2 mg to 20 mg of olanzapine, 0.2 mg to 10 mg trifluoperazine, 0.2 mg to 10 mg of haloperidol, 2 mg to 100 mg of loxapine, 0.1 mg to 5 mg of risperidone, 2 mg to 200 mg of clozapine, 2 mg to 200 mg of quetiapine, 2 mg to 200 mg of promazine, 0.5 mg to 20 mg of thiothixene, 2 mg to 200 mg of chlorpromazine, 0.2 mg to 20 mg of droperidol, 0.5 mg to 20 mg of prochlorperazine, and 0.1 mg to 10 mg of fluphenazine are generally provided per inspiration for the same indication. A typical dosage of an antipsychotic containing aerosol is either administered as a single inhalation or as a series of inhalations taken within an hour or less (dosage equals sum of inhaled amounts). Where the drug is administered as a series of inhalations, a different amount may be delivered in each inhalation.

One can determine the appropriate dose of antipsychotic containing aerosols to treat a particular condition using methods such as animal experiments and a dose-finding (Phase I/II) clinical trial. One animal experiment involves measuring plasma concentrations of drug in an animal after its exposure to the aerosol. Mammals such as dogs or primates are typically used in such studies, since their respiratory systems are similar to that of a human. Initial dose levels for testing in humans is generally less than or equal to the dose in the mammal model that resulted in plasma drug levels associated with a therapeutic effect in humans. Dose escalation in humans is then performed, until either an optimal therapeutic response is obtained or a dose-limiting toxicity is encountered.

Analysis of Antipsychotic Containing Aerosols

Purity of an antipsychotic containing aerosol is determined using a number of methods, examples of which are described in Sekine et al., *Journal of Forensic Science* 32:1271-1280 (1987) and Martin et al., *Journal of Analytic Toxicology* 13:158-162 (1989). One method involves forming the aerosol in a device through which a gas flow (e.g., air flow) is maintained, generally at a rate between 0.4 and 60 L/min. The gas flow carries the aerosol into one or more traps. After isolation from the trap, the aerosol is subjected to an analytical technique, such as gas or liquid chromatography, that permits a determination of composition purity.

A variety of different traps are used for aerosol collection. The following list contains examples of such traps: filters; glass wool; impingers; solvent traps, such as dry ice-cooled ethanol, methanol, acetone and dichloromethane traps at various pH values; syringes that sample the aerosol; empty, low-pressure (e.g., vacuum) containers into which the aerosol is drawn; and, empty containers that fully surround and enclose the aerosol generating device. Where a solid such as glass wool is used, it is typically extracted with a solvent such as ethanol. The solvent extract is subjected to analysis rather than the solid (i.e., glass wool) itself. Where a syringe or container is used, the container is similarly extracted with a solvent.

The gas or liquid chromatograph discussed above contains a detection system (i.e., detector). Such detection systems are well known in the art and include, for example, flame ionization, photon absorption and mass spectrometry detectors. An advantage of a mass spectrometry detector is that it can be used to determine the structure of antipsychotic degradation products.

Particle size distribution of an antipsychotic containing aerosol is determined using any suitable method in the art (e.g., cascade impaction). An Andersen Eight Stage Non-viable Cascade Impactor (Andersen Instruments, Smyrna, Ga.) linked to a furnace tube by a mock throat (USP throat, Andersen Instruments, Smyrna, Ga.) is one system used for cascade impaction studies.

Inhalable aerosol mass density is determined, for example, by delivering a drug-containing aerosol into a confined chamber via an inhalation device and measuring the mass collected in the chamber. Typically, the aerosol is drawn into the chamber by having a pressure gradient between the device and the chamber, wherein the chamber is at lower pressure than the device. The volume of the chamber should approximate the tidal volume of an inhaling patient.

Inhalable aerosol drug mass density is determined, for example, by delivering a drug-containing aerosol into a confined chamber via an inhalation device and measuring the amount of active drug compound collected in the chamber. Typically, the aerosol is drawn into the chamber by having a pressure gradient between the device and the chamber, wherein the chamber is at lower pressure than the device. The volume of the chamber should approximate the tidal volume of an inhaling patient. The amount of active drug compound collected in the chamber is determined by extracting the chamber, conducting chromatographic analysis of the extract and comparing the results of the chromatographic analysis to those of a standard containing known amounts of drug.

Inhalable aerosol particle density is determined, for example, by delivering aerosol phase drug into a confined chamber via an inhalation device and measuring the number of particles of given size collected in the chamber. The number of particles of a given size may be directly measured based on the light-scattering properties of the particles. Alternatively, the number of particles of a given size is determined by measuring the mass of particles within the given size range and calculating the number of particles based on the mass as follows: Total number of particles=Sum (from size range 1 to size range N) of number of particles in each size range. Number of particles in a given size range=Mass in the size range/Mass of a typical particle in the size range. Mass of a typical particle in a given size range=$\pi^*D^3{}^*\phi/6$, where D is a typical particle diameter in the size range (generally, the mean boundary MMADs defining the size range) in microns, $\phi$ is the particle density (in g/mL) and mass is given in units of picograms ($g^{-12}$).

Rate of inhalable aerosol particle formation is determined, for example, by delivering aerosol phase drug into a confined chamber via an inhalation device. The delivery is for a set period of time (e.g., 3 s), and the number of particles of a given size collected in the chamber is determined as outlined above. The rate of particle formation is equal to the number of 100 nm to 5 micron particles collected divided by the duration of the collection time.

Rate of aerosol formation is determined, for example, by delivering aerosol phase drug into a confined chamber via an inhalation device. The delivery is for a set period of time (e.g., 3 s), and the mass of particulate matter collected is determined by weighing the confined chamber before and after the delivery of the particulate matter. The rate of aerosol formation is equal to the increase in mass in the chamber divided by the duration of the collection time. Alternatively, where a change in mass of the delivery device or component thereof can only occur through release of the aerosol phase particulate matter, the mass of particulate matter may be equated with the mass lost from the device or component during the delivery of the aerosol. In this case, the rate of aerosol formation is equal to the decrease in mass of the device or component during the delivery event divided by the duration of the delivery event.

Rate of drug aerosol formation is determined, for example, by delivering an antipsychotic containing aerosol into a confined chamber via an inhalation device over a set period of time (e.g., 3 s). Where the aerosol is pure antipsychotic, the amount of drug collected in the chamber is measured as described above. The rate of drug aerosol formation is equal to the amount of antipsychotic collected in the chamber divided by the duration of the collection time. Where the antipsychotic containing aerosol comprises a pharmaceutically acceptable excipient, multiplying the rate of aerosol formation by the percentage of antipsychotic in the aerosol provides the rate of drug aerosol formation.

Utility of Antipsychotic Containing Aerosols

The antipsychotic containing aerosols of the present invention are typically used for the treatment of psychosis.

The following examples are meant to illustrate, rather than limit, the present invention.

Trifluoperazine, haloperidol, loxapine, quetiapine, promazine, thiothixene, chlorpromazine, droperidol, prochlorperazine dimaleate, and fluphenazine were purchased from Sigma. Risperidone was purchased from Sigma RBI. Quetiapine was purchased as SEROQUEL® tablets from a pharmacy. Clozapine and olanzapine were received as gifts from Reddy/Cheminor. Clozapine and olanzapine are also commercially available (isolation using standard methods in the art from CLOZARIL® and ZYPREXA® respectively). Other antipsychotics can be similarly obtained.

Example 1

General Procedure for Obtaining Free Base of a Compound Salt

Approximately 1 g of salt (e.g., mono hydrochloride) is dissolved in deionized water (~30 mL). Three equivalents of sodium hydroxide (1 N NaOH$_{aq}$) is added dropwise to the solution, and the pH is checked to ensure it is basic. The aqueous solution is extracted four times with dichloromethane (~50 mL), and the extracts are combined, dried (Na$_2$SO$_4$) and filtered. The filtered organic solution is concentrated using a rotary evaporator to provide the desired free base. If necessary, purification of the free base is performed using standard methods such as chromatography or recrystallization.

Example 2

General Procedure for Volatizing Compounds from Halogen Bulb

A solution of drug in approximately 120 µL dichloromethane is coated on a 3.5 cm×7.5 cm piece of aluminum foil (precleaned with acetone). The dichloromethane is allowed to evaporate. The coated foil is wrapped around a 300 watt halogen tube (Feit Electric Company, Pico Rivera, Calif.), which is inserted into a glass tube sealed at one end with a rubber stopper. Running 90 V or 108 V (prochlorperazine) of alternating current (driven by line power controlled by a variac) through the bulb for 3.5 s or 2.25 s (prochlorperazine) (drug coating of 0.01 mg to 8 mg) or for 5 s (drug coating>8 mg) affords thermal vapor (including aerosol), which is collected on the glass tube walls. Reverse-phase HPLC analysis with detection by absorption of 225 nm light is used to determine the purity of the aerosol. (When desired, the system is flushed through with argon prior to volatilization.) To obtain higher purity aerosols, one can coat a lesser amount of drug, yielding a thinner film to heat. A linear decrease in film thickness is associated with a linear decrease in impurities.

Table 1, which follows, provides data from drugs volatilized using the above-recited general procedure.

TABLE 1

| Compound | Aerosol Purity | Argon Used |
|---|---|---|
| Promazine | 97.5% | No |
|  | 98.3% | Yes |
| Olanzapine | 100% | No |
|  | 99.7% | Yes |
| Trifluoperazine | 98% | No |
|  | 98% | Yes |
| Chlorpromazine | 96.5% | No |
|  | 97% | Yes |
| Clozapine | 99.1% | No |
|  | 99.5% | Yes |
| Fluphenazine | 93% | No |
|  | 95% | Yes |
| Haloperidol | 96% | No |
|  | 97% | Yes |
| Loxapine | 99.3 | No |
|  | 99.7 | Yes |
| Quetiapine | 99.7% | No |
| Prochlorperazine | 97.5% | No |

Example 3

Particle Size, Particle Density, and Rate of Inhalable Particle Formation of Olanzapine Aerosol A solution of 12.9 mg olanzapine in 200 µL dichloromethane was spread out in a thin layer on the central portion of a 3.5 cm×7 cm sheet of aluminum foil. The dichloromethane was allowed to evaporate. The aluminum foil was wrapped around a 300 watt halogen tube, which was inserted into a T-shaped glass tube. Both of the openings of the tube were sealed with parafilm, which was punctured with fifteen needles for flow. The third opening was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within 1 s, an aerosol appeared and was drawn into the 1 L flask by use of the piston, with collection of the aerosol terminated after 6 s. The aerosol was analyzed by connecting the 1 L flask to an eight-stage Andersen non-viable cascade impactor. Results are shown in table 1. MMAD of the collected aerosol was 1.6 microns with a geometric standard deviation of 1.7. Also shown in table 1 is the number of particles collected on the various stages of the cascade impactor, given by the mass collected on the stage divided by the mass of a typical particle trapped on that stage. The mass of a single particle of diameter D is given by the volume of the particle, $\pi D^3/6$, multiplied by the density of the drug (taken to be 1 g/cm$^3$). The inhalable aerosol particle density is the sum of the numbers of particles collected on impactor stages 3 to 8 divided by the collection volume of 1 L, giving an inhalable aerosol particle density of 4.5×10$^6$ particles/mL. The rate of inhalable aerosol particle formation is the sum of the numbers of particles collected on impactor stages 3 through 8 divided by the formation time of 6 s, giving a rate of inhalable aerosol particle formation of 7.6×10$^8$ particles/second.

Table 1: Determination of the characteristics of a olanzapine condensation aerosol by cascade impaction using an Andersen 8-stage non-viable cascade impactor run at 1 cubic foot per minute air flow.

| Stage | Particle size range (microns) | Average particle size (microns) | Mass collected (mg) | Number of particles |
|---|---|---|---|---|
| 0 | 9.0-10.0 | 9.5 | 0.1 | $2.2 \times 10^5$ |
| 1 | 5.8-9.0 | 7.4 | 0.0 | 0 |
| 2 | 4.7-5.8 | 5.25 | 0.0 | 0 |
| 3 | 3.3-4.7 | 4.0 | 0.1 | $3.0 \times 10^6$ |
| 4 | 2.1-3.3 | 2.7 | 0.9 | $8.7 \times 10^7$ |
| 5 | 1.1-2.1 | 1.6 | 2.0 | $9.3 \times 10^8$ |
| 6 | 0.7-1.1 | 0.9 | 0.9 | $2.4 \times 10^9$ |
| 7 | 0.4-0.7 | 0.55 | 0.1 | $1.2 \times 10^9$ |
| 8 | 0-0.4 | 0.2 | 0.0 | 0 |

Example 4

Drug Mass Density and Rate of Drug Aerosol Formation of Olanzapine Aerosol

A solution of 11.3 mg olanzapine in 200 µL dichloromethane was spread out in a thin layer on the central portion of a 3.5 cm×7 cm sheet of aluminum foil. The dichloromethane was allowed to evaporate. The aluminum foil was wrapped around a 300 watt halogen tube, which was inserted into a T-shaped glass tube. Both of the openings of the tube were sealed with parafilm, which was punctured with fifteen needles for flow. The third opening was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within seconds, an aerosol appeared and was drawn into the 1 L flask by use of the piston, with formation of the aerosol terminated after 6 s. The aerosol was allowed to sediment onto the walls of the 1 L flask for approximately 30 minutes. The flask was then extracted with acetonitrile and the extract analyzed by HPLC with detection by light absorption at 225 nm. Comparison with standards containing known amounts of olanzapine revealed that 1.2 mg of >99% pure olanzapine had been collected in the flask, resulting in an aerosol drug mass density of 1.2 mg/L. The aluminum foil upon which the olanzapine had previously been coated was weighed following the experiment. Of the 11.3 mg originally coated on the aluminum, 7.1 mg of the material was found to have aerosolized in the 6 s time period, implying a rate of drug aerosol formation of 1.2 mg/s.

The invention claimed is:

1. An aerosol for delivery of loxapine by inhalation comprising condensation particles having an MMAD of 0.2 to 5 microns and a high particle concentration of the condensation particles.

2. The aerosol of claim 1, wherein the aerosol is at least 90% free of additional compounds.

3. The aerosol of claim 1, wherein the condensation particles have and MMAD of 1-3 microns.

4. The aerosol of claim 1, wherein the high particle concentration of the condensation particles is about $10^9$ particles/ml.

5. An aerosol for delivery of loxapine by inhalation comprising condensation particles having an MMAD of 0.2 to 5 microns and a particle density greater than $10^6$ particles/ml.

6. The aerosol of claim 5, wherein the aerosol is at least 90% free of additional compounds.

7. The aerosol of claim 5, wherein the condensation particles have an MMAD of 1-3 microns.

8. The aerosol of claim 5, wherein the aerosol has a particle density of about $10^9$ particles/ml.

* * * * *